United States Patent
Hofmann (10) Patent No.: US 7,414,044 B2
(45) Date of Patent: *Aug. 19, 2008

(54) USE OF TARGETED OXIDATIVE THERAPEUTIC FORMULATION IN TREATMENT OF TYPE 2 DIABETES

(76) Inventor: Robert F. Hofmann, 3105 Toro Ring, Austin, TX (US) 78746-2432

( * ) Notice: Subject to any disclaimer, the term of this patent is extended or adjusted under 35 U.S.C. 154(b) by 131 days.

This patent is subject to a terminal disclaimer.

(21) Appl. No.: 11/122,907

(22) Filed: May 5, 2005

(65) Prior Publication Data

US 2005/0272714 A1    Dec. 8, 2005

Related U.S. Application Data

(60) Provisional application No. 60/568,542, filed on May 6, 2004.

(51) Int. Cl.
*A61K 31/555* (2006.01)
*A61K 31/20* (2006.01)
*A61K 31/045* (2006.01)

(52) U.S. Cl. .................. 514/185; 514/558; 514/724; 514/866

(58) Field of Classification Search ................ 514/185, 514/558, 866, 724
See application file for complete search history.

(56) References Cited

U.S. PATENT DOCUMENTS

| | | | |
|---|---|---|---|
| 4,451,480 A | 5/1984 | DeVillez | |
| 4,591,602 A | 5/1986 | DeVillez | |
| 4,983,637 A | 1/1991 | Herman | |
| 5,086,076 A | 2/1992 | Herman | |
| 5,126,376 A | 6/1992 | Herman | |
| 5,190,977 A | 3/1993 | Herman | |
| 5,190,979 A | 3/1993 | Herman | |
| 5,260,342 A | 11/1993 | Herman | |
| 5,270,344 A | 12/1993 | Herman | |
| 5,364,879 A | 11/1994 | Herman | |
| 6,187,333 B1 * | 2/2001 | Murad et al. ............. 424/436 | |
| 6,784,207 B2 * | 8/2004 | Fluehmann et al. ........ 514/560 | |
| 6,790,463 B2 * | 9/2004 | Hofmann et al. ........... 424/613 | |
| 6,884,797 B2 * | 4/2005 | Hofmann .................... 514/185 | |
| 2002/0082298 A1 * | 6/2002 | Fluehmann et al. ......... 514/558 | |
| 2002/0177585 A1 | 11/2002 | Hofmann et al. | |
| 2003/0032677 A1 | 2/2003 | Hofmann | |
| 2005/0110484 A1 | 5/2005 | Hofmann | |
| 2006/0002302 A1 | 1/2006 | Hofmann | |

OTHER PUBLICATIONS

National Diabetes Information Clearinghouse (NDIC), http://diabetes.niddk.nih.gov/dm/pubs/overview/index.htm. (2007).*
Cortez, M., C. Torgan, J. J. Brozinick, and J. Ivy. Insulin resistance of obese Zucker rats exercise trained at two different intensities. Am. J. Physiol 261: E613-619, 1991.
Crettaz, M., M. Prentki, D. Zaninetti, and B. Jeanrenaud. Insulin resistance in soleus muscle from obese Zucker rats: Involvement of several defective sites. Biochem. J. 186: 525-534, 1980.
Ivy, J.L., T.W. Zderic, and D.L. Fogt. Prevention and treatment of non-insulin-dependent diabetes mellitus. E.S.S.R. vol. 27, 1-35, 1999.
Ivy, J., W. Sherman, C. Cutler, and A. Katz. Exercise and diet reduce muscle insulin resistance in obese Zucker rat. Am. J. Physiol 251: E299-305, 1986.
Maritim A.C., R.A. Sanders, J.B. Watkins 3rd. Diabetes, oxidative stress, and antioxidants: A review. J. Biochem. Mol. Toxicol. 17: 24-38, 2003.
Sherman, W., A. Katz, C. Cutler, R. Withers, and J. Ivy. Glucose transport: locus of muscle insulin resistance in obese Zucker rats. Am. J. Physiol. 255: E374-382, 1988.
Zucker, L.M. and H.N. Antoniades. Insulin and obesity in the Zucker genetically obese Rat "fatty." Endocrinology 90: 1320-1330, 1972.
PCT Notification of Transmittal of the International Search Report and the Written Opinion of the International Searching Authority, or the Declaration dated Sep. 9, 2006.

* cited by examiner

*Primary Examiner*—Kevin E Weddington
(74) *Attorney, Agent, or Firm*—Jackson Walker L.L.P.

(57) ABSTRACT

A pharmaceutical formulation and its use. The pharmaceutical formulation contains peroxidic species or reaction products resulting from oxidation of an alkene, such as geraniol, by an oxygen-containing oxidizing agent, such as ozone; a penetrating solvent, such as dimethylsulfoxide ("DMSO"); a dye containing a chelated metal, such as hematoporphyrin; and an aromatic redox compound, such as benzoquinone. The pharmaceutical formulation is used to effectively treat patients affected with diabetes and obesity.

12 Claims, 5 Drawing Sheets

USE OF TARGETED OXIDATIVE THERAPEUTIC FORMULATION IN TREATMENT OF TYPE 2 DIABETES

This application claims priority to U.S. Provisional Patent Application Ser. No. 60/568,542, entitled "Use of Targeted Oxidative Therapeutic Formulation in Treatment of Diabetes and Obesity," filed on May 6, 2004, the entire content of which is hereby incorporated by reference.

BACKGROUND

The present invention relates to a composition containing peroxidic species or oxidation products, its method of preparation, and its use. More specifically, the invention relates to a pharmaceutical composition or formulation which contains: peroxidic species or reaction products resulting from oxidation of an olefinic compound, in a liquid form or in a solution, by an oxygen-containing oxidizing agent; a penetrating solvent; a dye containing a chelated metal; and an aromatic redox compound. The invention also relates to the preparation of the pharmaceutical formulation and its use in treating diabetes and obesity.

Ozone is a triatomic gas molecule and an allotropic form of oxygen. It may be obtained by means of an electrical discharge or intense ultraviolet light through pure oxygen. The popular misconception that ozone is a serious pollutant, the "free radical" theory of disease, and the antioxidant supplement market have comprehensibly prejudiced medical orthodoxy against its use as a treatment. Ozone therapy, however, is a misnomer. Ozone is an extremely reactive and unstable gas with mechanisms of action directly related to the by-products that it generates through selective interaction with organic compounds present in the plasma and in the cellular membranes. The selective reaction of ozone with unsaturated olefins occurs at the carbon—carbon double bond, generating ozonides. Ozone is toxic by itself, and its reaction products, ozonides, are unstable and are not therapeutic by themselves.

Hydrogen peroxide ($H_2O_2$), discovered in 1818, is present in nature in trace amounts. Hydrogen peroxide is unstable and decomposes violently (or foams) when in direct contact with organic membranes and particulate matter. Light, agitation, heating, and iron all accelerate the rate of hydrogen peroxide decomposition in solution. Hydrogen peroxide by direct contact ex vivo kills microbes that have low levels of peroxide-destroying enzymes, such as the catalases. However, there is no bactericidal effect when hydrogen peroxide is infused into the blood of rabbits infected with peroxide-sensitive E. coli. Moreover, increasing the concentration of peroxide ex-vivo in rabbit or human blood containing E. coli produces no evidence of direct bactericidal activity. The lack of effect of high concentrations of hydrogen peroxide is directly related to the presence of the peroxide-destroying enzyme catalase in the host animal's blood. To have any effect, high concentrations of hydrogen peroxide have to be in contact with the bacteria for significant periods of time. Large amounts of hydrogen peroxide-destroying enzymes, such as catalase, normally present in the blood make it impossible for peroxide to exist in blood for more than a few seconds. Thus, hydrogen peroxide introduced into the blood stream by injection or infusion does not directly act as an extracellular germicide in blood or extracellular fluids.

However, hydrogen peroxide does participate in the bactericidal processes of activated macrophage cells. Activated macrophage cells are drawn to the site of infection, attach to the infectious organism, and ingest it. The killing of the organisms takes place inside the macrophage cell by hydrogen peroxide. Hydrogen peroxide oxidizes cellular chloride to the chlorine dioxide free radical, which destabilizes microbial membranes and, if persistent, induces apoptosis or cellular suicide. The critical therapeutic criteria for intracellular peroxidation are the selective delivery, absorption and activation of peroxidic carrier molecules into only diseased macrophages, which are believed to be incapable of upgraded catalase and glutathione reductase activity. Infused hydrogen peroxide is a generalized poison whereas targeted intracellular peroxidation is a selective therapeutic tool.

Macrophage cells play critical roles in immunity, bone calcification, vision, neural insulation (myelinization), detoxification, pump strength, and clearance of toxins from the body, depending upon their site of localization. The energy requirements of macrophages are met by intracellular structures called mitochondria. Mitochondria are often structurally associated with the microfilament internal cytoarchitecture. The folded internal layer of the mitochondria creates the high-energy molecule ATP, while the outer layer contains cytochromes and electron recycling molecules that generate peroxides. The outer layers of mitochondria are susceptible to toxic blockade or damage by endotoxins, mycotoxins, drugs, heavy metals, and pesticides. When the peroxidation function of mitochondria is blocked, the filament architecture of the cell tends to cross-link, generating incorrect signals, incompetence, inappropriate replication, or premature cell death.

Type 2 diabetes develops when tissue responsible for the regulation of blood glucose becomes resistant to insulin (Ivy, et al., 1999). Insulin resistance is evident when a normal insulin concentration produces a less than normal biological response. Skeletal muscle is the primary tissue responsible for control of blood glucose in the post-prandial state when insulin levels are elevated.

Increasing evidence in both experimental and clinical studies suggests that an oxidation-reduction imbalance plays a major role in the pathogenesis of both types of diabetes mellitus (Maritim, et al., 2003). Diabetes-affected individuals may experience such imbalance during glucose oxidation, nonenzymatic glycation of proteins, and the subsequent oxidative degradation of glycated proteins, and it can lead to damage of cellular organelles and enzymes, increased lipid peroxidation, and the development of insulin resistance. These consequences of an oxidation-reduction imbalance can promote the development of complications of diabetes mellitus.

Insulin resistance is also a common feature in most types of human and animal obesities. Skeletal muscle is unable to clear glucose from the circulation when there is a lack of insulin-stimulated muscle glucose uptake. Excess glucose in the blood is then converted to fat cells, which over time results in obesity. Thus, reducing whole body insulin resistance would effectively treat obesity by improving skeletal muscle glucose uptake and decreasing excess glucose in the circulation.

U.S. Pat. No. 4,451,480 to De Villez teaches a composition and method for treating acne. The method includes topically treating the affected area with an ozonized material derived from ozonizing various fixed oil and unsaturated esters, alcohols, ethers and fatty acids.

U.S. Pat. No. 4,591,602 to De Villez shows an ozonide of Jojoba used to control microbial infections.

U.S. Pat. No. 4,983,637 to Herman discloses a method to parenterally treat local and systemic viral infections by administering ozonides of terpenes in a pharmaceutically acceptable carrier.

U.S. Pat. No. 5,086,076 to Herman shows an antiviral composition containing a carrier and an ozonide of a terpene. The composition is suitable for systemic administration or local application.

U.S. Pat. No. 5,126,376 to Herman describes a method to topically treat a viral infection in a mammal using an ozonide of a terpene in a carrier.

U.S. Pat. No. 5,190,977 to Herman teaches an antiviral composition containing a non-aqueous carrier and an ozonide of a terpene suitable for systemic injection.

U.S. Pat. No. 5,190,979 to Herman describes a method to parenterally treat a medical condition in a mammal using an ozonide of a terpene in a carrier.

U.S. Pat. No. 5,260,342 to Herman teaches a method to parenterally treat viral infections in a mammal using an ozonide of a terpene in a carrier.

U.S. Pat. No. 5,270,344 to Herman shows a method to treat a systemic disorder in a mammal by applying to the intestine of the mammal a trioxolane or a diperoxide derivative of an unsaturated hydrocarbon which derivative is prepared by ozonizing the unsaturated hydrocarbon dissolved in a non-polar solvent.

U.S. Pat. No. 5,364,879 to Herman describes a composition for the treatment of a medical condition in a mammal, the composition contains a diperoxide or trioxolane derivative of a non-terpene unsaturated hydrocarbon which derivative is prepared by ozonizing below 35° C. the unsaturated hydrocarbon in a carrier.

Despite the reports on the use of terpene ozonides for different medical indications, terpene ozonides display multiple deficiencies. For example, ozonides of monoterpene, such as myrcene and limonene, flamed out in the laboratory. Consequently, they are extremely dangerous to formulate or store.

Furthermore, ozonides of geraniol, a linear monoterpene alcohol, in water or in dimethylsulfoxide ("DMSO") did not show any clinical efficacy in three cases of viral Varicella Zoster (shingles) and two cases of Herpes Simplex dermatitis.

Thus, there is a need for a safe and effective pharmaceutical formulation or composition utilizing reaction products from the oxidation of an alkene compound. What is also needed is a method for stimulating mitochondrial defenses against free radical formation and reducing the insulin resistance of diabetes-affected and obese individuals.

SUMMARY

This invention is directed to pharmaceutical formulations comprising peroxidic species or reaction products resulting from oxidation of an unsaturated organic compound, in a liquid form or in a solution, by an oxygen-containing oxidizing agent; a penetrating solvent; a chelated dye; and an aromatic redox compound. In one embodiment of the pharmaceutical formulation, the essential components include the peroxidic products formed by ozonolysis of an unsaturated alcohol, a stabilizing solvent, metalloporphyrin, and quinone. This invention is also directed to use of the pharmaceutical formulation to treat diabetes and obesity.

The peroxidic species or reaction products are preferably formed through the reaction of an alkene and ozone. It is generally accepted that the reaction between an alkene and ozone proceeds by the Criegee mechanism. According to this mechanism, shown in Scheme 1 below, the initial step of the reaction is a 1,3-dipolar cycloaddition of ozone to the alkene to give a primary ozonide (a 1,2,3-trioxalane). The primary ozonide is unstable, and undergoes a 1,3-cycloreversion to a carbonyl compound and a carbonyl oxide. In the absence of other reagents or a nucleophilic solvent, this new 1,3-dipole enters into a second 1,3-dipolar cycloaddition to give the "normal" ozonide, a 1,2,4-trioxalane.

SCHEME 1

In a side reaction, the carbonyl oxide can enter into a dimerization to give a peroxidic dimer, the 1,2,4,5-tetraoxane, shown in Scheme 2 below.

SCHEME 2

The carbonyl oxide is a strongly electrophilic species, and in the presence of nucleophilic species (e.g. alcohols or water), it undergoes facile nucleophilic addition to give a 1-alkoxyhydroperoxide, shown in Scheme 3 below. Under certain conditions, the 1-alkoxyhydroperoxide can undergo further reaction to give carboxylic acid derivatives.

SCHEME 3

Again, not wanting to be bound by theory, it is believed that during the ozonolysis of the alcohol-containing alkene in the present invention, it is reasonable to expect that three major types of peroxidic products will be present: the normal ozonide, the carbonyl tetraoxane dimer, and the 1-alkoxyhydroperoxide. In the presence of water, some of these peroxidic products may also lead to the presence of organic peracids in the crude product mixture.

The present invention also involves the use of a penetrating solvent such as dimethylsulfoxide ("DMSO") to "stabilize" the initial products of the ozonolysis. Similarly, not wanting to be bound by any theory, it is believed that the stabilization is most likely a simple solvation phenomenon. However, DMSO is known to be a nucleophile in its own right. Its participation is also possible as a nucleophilic partner in stabilizing reactive species (for example, as dimethylsulfoxonium salts). The stabilized peroxidic molecule and the penetrating solvent of the current pharmaceutical formulation are made from components generally regarded as safe ("GRAS").

Another component of the pharmaceutical formulation is a chelated dye, such as a porphyrin. The propensity of metalloporphyrins to sensitize oxygen under photochemical excitation is well documented, as is the propensity of ferroporphyrins and copper porphyrins to bind oxygen-containing systems.

A further component of the pharmaceutical formulation is an aromatic redox compound, such as a quinone.

Although not wanting to be bound by any theory, it is postulated that the preferred pharmaceutical formulation is a combination of biochemical agents that induce recycling autocatalytic oxidation in infected or dysplastic macrophages. The pharmaceutical formulation stimulates targeted apoptosis (cell suicide) through unopposed peroxidation. Thus, the pharmaceutical formulation creates therapeutic effects in a number of seemingly disparate mitochondria-based macrophagic diseases. In particular, the pharmaceutical formulation has been shown to be effective in reducing whole body insulin resistance, lowering blood glucose response, and improving muscle glucose uptake, which indicates its effectiveness at treating diabetes and obesity.

DETAILED DESCRIPTION OF PREFERRED EMBODIMENTS

The current invention pertains to pharmaceutical formulations comprising peroxidic species or reaction products resulting from oxidation of an unsaturated organic compound, in a liquid form or in a solution, by an oxygen-containing oxidizing agent; a penetrating solvent; a chelated dye; and an aromatic redox compound. The pharmaceutical formulations may be used to treat diabetes and obesity. In one embodiment of the present invention, the essential components of the pharmaceutical formulation include the peroxidic products formed by ozonolysis of an unsaturated alcohol, a stabilizing solvent, metalloporphyrin, and quinone.

The unsaturated organic compound, which may also be an unsaturated olefinic hydrocarbon, of the pharmaceutical formulation can be an alkene without a hydroxyl group, or a hydroxyl-containing alkene. Preferably, the alkene has less than about 35 carbons. The alkene without a hydroxyl group may be an open-chain unsaturated hydrocarbon, a monocyclic unsaturated hydrocarbon, or a bicyclic unsaturated hydrocarbon. The hydroxyl-containing alkene can be an open-chain unsaturated alcohol, a monocyclic unsaturated alcohol, or a bicyclic unsaturated alcohol. The alkene may also be contained in a fixed oil, an ester, a fatty acid, or an ether.

Usable unsaturated olefinic hydrocarbons may be unsubstituted, substituted, cyclic or complexed alkenes, hydrazines, isoprenoids, steroids, quinolines, carotenoids, tocopherols, prenylated proteins, or unsaturated fats. The preferred unsaturated hydrocarbons for this invention are alkenes and isoprenoids.

Isoprenoids are found primarily in plants as constituents of essential oils. While many isoprenoids are hydrocarbons, oxygen-containing isoprenoids also occur such as alcohols, aldehydes, and ketones. In a formal sense, the building block of isoprenoid hydrocarbons may be envisaged as the hydrocarbon isoprene, $CH_2$=$C(CH_3)$—$CH$=$CH_2$, although it is known that isoprene itself is an end-product of isoprenoid biosynthesis and not an intermediate. Isoprenoid hydrocarbons are categorized by the number of isoprene ($C_5H_8$) units they contain. Thus, monoterpenes have 2, sesquiterpenes have 3, diterpenes have 4, sesterterpenes have 5, triterpenes have 6, and tetraterpenes have 8 isoprene units, respectively. Tetraterpenes are much more commonly known as carotenoids.

Limonene and pinene are examples of a monoterpene. Farnesol and nerolidol are examples of a sesquiterpene alcohol. Vitamin $A_1$ and phytol are examples of a diterpene alcohol while squalene is an example of a triterpene. Provitamin $A_1$, known as carotene, is an example of a tetraterpene. Geraniol, a monoterpene alcohol, is liquid in both its oxygen bound and normal states and is safe to living cells.

Preferred unsaturated hydrocarbons for the pharmaceutical formulation include alkene isoprenoids, such as myricene, citrillene, citral, pinene, or limonene. Preferred unsaturated hydrocarbons also include linear isoprenoid alcohols with two to four repeating isoprene groups in a linear chain, such as α-terpineol, citronellol, nerol, phytol, menthol, geraniol, geranylgeraniol, linalool, or farnesol.

The unsaturated organic compound may be linear, branched, cyclic, spiral, or complexed with other molecules in its configuration. The unsaturated organic compound may naturally exist in a gaseous liquid or solid state prior to binding with the oxidizing agent.

An open-chain unsaturated hydrocarbon can be: $C_nH_{2n}$, one double bond, n=2-20; $C_nH_{2n-2}$, two double bonds, n=4-20; $C_nH_{2n-4}$, three double bonds, n=6-20; $C_nH_{2n-6}$, four double bonds, n=8-20; $C_{25}H_{40}$, sesterterpene hydrocarbon; or $C_{30}H_{48}$, triterpene hydrocarbon.

A monocyclic unsaturated hydrocarbon can be: $C_nH_{2n-2}$, one double bond and one ring, n=3-20; $C_nH_{2n-4}$, two double bonds and one ring, n=5-20; $C_nH_{2n-6}$, three double bonds and one ring, n=7-20; $C_{25}H_{40}$, sesterterpene hydrocarbon; or $C_{30}H_{48}$, triterpene hydrocarbon.

A bicyclic unsaturated hydrocarbon can be: $C_nH_{2n-4}$, one double bond and two rings, n=4-20; $C_nH_{2n-6}$, two double bonds and two rings, n=6-20; $C_{25}H_{40}$, sesterterpene hydrocarbon; or $C_{30}H_{48}$, triterpene hydrocarbons.

An open-chain unsaturated alcohol can be: $C_nH_{2n}O_m$, one double bond, n=3-20, m=1-4; $C_nH_{2n-2}O_m$, two double bonds, n=5-20, m=1-4; $C_nH_{2n-4}O_m$, three double bonds, n=7-20, m=1-4; $C_nH_{2n-6}O_m$, four double bonds, n=9-20, m=1-4; $C_{25}H_{40}O_m$, m=1-4, sesterterpene alcohols; or $C_{30}H_{48}O_m$, m=1-4, triterpene alcohols.

A monocyclic unsaturated alcohol can be: $C_nH_{2n-2}O_m$, one double bond and one ring, n=3-20, m=1-4; $C_nH_{2n-4}O_m$, two double bonds and one ring, n=5-20, m=1-4; $C_nH_{2n-6}O_m$, three double bonds+one ring, n=7-20, m=1-4; $C_{25}H_{40}O_m$, m=1-4, sesterterpene alcohols; or $C_{30}H_{48}O_m$, m=1-4, triterpene alcohols.

A bicyclic unsaturate alcohol can be: $C_nH_{2n-4}O_m$, one double bond and two rings, n=5-20, m=1-4; $C_nH_{2n-6}O_m$, two double bonds and two rings, n=7-20, m=1-4; $C_{25}H_{40}O_m$, m=1-4, sesterterpene alcohols; or $C_{30}H_{48}O_m$, m=1-4, triterpene alcohols.

Based on the total weight of the pharmaceutical formulation, the alkene can vary from about 0.001% to about 30%, preferably from about 0.1% to about 5.0%, and more preferably from about 0.5% to about 3.0%.

The oxygen-containing oxidizing agent of the pharmaceutical formulation, which oxidizes the unsaturated hydrocarbon, maybe singlet oxygen, oxygen in its triplet state, superoxide anion, ozone, periodate, hydroxyl radical, hydrogen peroxide, alkyl peroxide, carbamyl peroxide, benzoyl peroxide, or oxygen bound to a transition element, such as molybdenum (e.g. $MoO_5$).

The preferred method to bind "activated oxygen" to intact an isoprenoid alcohol, such as geraniol, is by ozonation at temperatures between 0-20° C. in the dark in the absence of water or polar solvent. The geraniol "ozonides" are then dissolved and stabilized in 100% DMSO in the dark to prevent premature breakdown of the products. Although not wanting to be bound by any theory, it is believed that the catalytic breakdown of the tetraoxane peroxidic dimer byproduct of geraniol ozonation, which is not an ozonide, occurs inside of cells in the presence of superoxide anion. The final reactive therapeutic agents released are hydrogen peroxide and acetic acid.

The pharmaceutical formulation also utilizes a penetrating solvent. The penetrating solvent, which stablizes the oxygen-bound unsaturated hydrocarbon, may be an emollient, a liquid, a micelle membrane, or a vapor. Usable penetrating solvents include aqueous solution, fats, sterols, lecithins, phosphatides, ethanol, propylene glycol, methylsulfonylmethane, polyvinylpyrrolidone, pH-buffered saline, and dimethylsulfoxide ("DMSO"). The preferred penetrating solvents include DMSO, polyvinylpyrrolidone, and pH-buffered saline. The most preferred penetrating solvent is DMSO.

Based on the total weight of the pharmaceutical formulation, the penetrating solvent can vary from about 50% to about 99%, preferably from about 90% to about 98%, and more preferably from about 95% to about 98%.

The "stabilized" peroxidic molecule and its penetrating solvent have been made from components currently used in production regulated by the Food and Drug Administration ("FDA"). These ingredients are the subject of Drug Master Files, Drug Monographs, are found in the USP/NF, or are Generally Recognized As Safe ("GRAS").

Another component of the pharmaceutical formulation is a chelated dye. The dye preferably contains a chelated divalent or trivalent metal, such as iron, copper, manganese tin, magnesium, or strontium. The preferred chelated metal is iron. The propensity of chelated dyes such as metalloporphyrins to sensitize oxygen under photochemical excitation is well documented, as is the propensity of ferroporphyrins and copper porphyrins to bind oxygen-containing systems. Usable dyes include natural or synthetic dyes. Examples of these dyes include porphyrins, rose bengal, chlorophyllins, hemins, porphins, corrins, texaphrins, methylene blue, hematoxylin, eosin, erythrosin, flavinoids, lactoflavin, anthracene dyes, hypericin, methylcholanthrene, neutral red, fluorescein, phthalocyanine, eumelanin, and pheomelanin. Preferred dyes can be any natural or synthetic porphyrin, hematoporphyrin, chlorophyllin, rose bengal, their respective congeners, or a mixture thereof. The most preferred dyes are naturally occurring porphyrins, such as hematoporphyrin, and rose bengal. The dye may be responsive to photon, laser, ionizing radiation, phonon, electrical cardiac electroporation, magnetic or plasma pulse, or continuous flow excitation.

Based on the total weight of the pharmaceutical formulation or composition, the dye can vary from about 0.1% to about 30%, preferably from about 0.5% to about 5%, and more preferably from about 0.8% to about 1.5%.

A further component of the pharmaceutical formulation is an aromatic redox compound, such as a quinone. The aromatic redox compound may be any substituted or unsubstituted benzoquinone, naphthoquinone, or anthroquinone. Preferred aromatic redox compounds include benzoquinone, methyl-benzoquinone, naphthoquinone, and methyl-naphthoquinone. The most preferred aromatic redox compound is methyl-naphthoquinone.

Based on the total weight of the pharmaceutical formulation, the aromatic redox compound can vary from about 0.01% to about 20.0%, preferably from about 0.1% to about 10%, and more preferably from about 0.1% to about 0.5%.

The pharmaceutical formulation is also preferably activated by an energy source or an electron donor. Useful electron donors include plasma, an electrical current, ascorbate or ascorbic acid, and germanium sesquioxide. Preferred electron donors include ascorbate and germanium sesquioxide. The most preferred electron donor is ascorbic acid in any salt form.

Based on the total weight of the pharmaceutical formulation, the electron donor can vary from about 0.01% to about 20%, preferably from about 1% to about 10%, and more preferably from about 1% to about 5%.

In order to obtain a biological effect in vivo, the pharmaceutical formulation is preferably infused as an ozonolysis-generated peroxidic product of an unsaturated hydrocarbon, rather than an ozonide, in conjunction with a superoxide generating chelated dye and an aromatic quinone. The unsaturated hydrocarbon product, or peroxidic dimer molecule, should be stabilized in a non-aqueous stabilizing solvent and should be capable of penetrating lipid membranes.

Researchers of energetically activated dye therapy have long known that the superoxide generating dye and the aromatic redox compound preferentially absorb into infected and dysplastic cells, which are typically also catalase deficient. Without wanting to be bound by theory, the catalase-induced destruction of peroxide should be overwhelmed in the target cells either naturally or by the pharmaceutical formulation. The peroxidic dimer should also be activated by the superoxide generating dye, initiating electron donation to the dimer and causing the release of hydrogen peroxide and acetic acid intracellularly. The electronic activation of the dye does not always require light, but rather may occur through small electrical pulses provided by, for example, a heart pulse. The peroxidation reaction within the infected macrophage then tends to destroy the prenylated protein linkage of microtubules within the cell, to destroy the infecting toxin, or to induce apoptosis of the macrophage host cell.

The pharmaceutical formulation is a combination of stable ingredients. These ingredients may preferably be stored as dry solid ingredients and liquid ingredients in separate containers, which are then mixed at the site of use. The dry solid ingredients preferably comprise the chelated dye and the aromatic redox compound. The liquid ingredients preferably comprise the peroxidic species or reaction products resulting from oxidation of the unsaturated hydrocarbon by the oxygen-containing active agent, along with the penetrating solvent. Administration is preferably intravenously. The reconstituted product preferably may be administered intravenously as a concentrate diluted in saline. Endodontic and intrathecal deliveries are also possible routes for administration. Intramuscular injection is not preferred, as it has a tendency to produce local irritation.

Administration of the pharmaceutical formulation in vivo is effective in reducing whole body insulin resistance, lowering blood glucose response, and improving muscle glucose uptake, which indicates its effectiveness at treating diabetes and obesity.

EXAMPLE 1

Ozonolysis of an Unsaturated Hydrocarbon

Ozonolysis of an alkene may be carried out either in a solvent or neat. In either case, the cooling of the reaction mixture is critical in avoiding explosive decomposition of the peroxidic products of the reaction.

The following general procedure is typical for the ozonolysis of a liquid alkene.

A 1-liter flask fitted with a magnetic stirrer is charged with the alkene (2 moles), and the apparatus is weighed. The flask is surrounded by a cooling bath (ice-water or ice-salt). Once the contents are cooled below 5° C., stirring is begun and a stream of ozone in dry oxygen (typically 3% ozone) is passed through the mixture. It is advantageous to disperse the ozonated oxygen through a glass frit, but this is not necessary for a stirred solution. Periodically, the gas stream is stopped, and the reaction flask is weighed or the reaction mixture is sampled. The gas stream is then re-started.

Once the mass of the reaction flask shows sufficient weight gain, or once the proton magnetic resonance ("$H^1$ NMR") spectrum of the reaction mixture shows the desired reduction in the intensity of the olefinic proton resonances (usually about 50%), the gas flow is stopped.

The ozonolysis may be carried out as above, substituting a solution of the alkene in a solvent non-reactive towards ozone such as saturated hydrocarbons or chlorinated hydrocarbons. The ozonolysis may also be carried out as above, with or without solvent, substituting an alkenol for the alkene without affecting the reaction in any substantive manner.

The reaction mixture is then poured slowly into the cooled penetrating solvent.

EXAMPLE 2

Preparation of the Pharmaceutical Formulation

A preferred pharmaceutical formulation of the present invention was prepared as follows:

(1) Sparging an ozone/pure oxygen gas mixture of 120 mg/L up through an alkadiene alcohol, 3,7-dimethyl-2,6-octadien-1-ol (geraniol), at 1 Liter of gas per hour;

(2) Maintaining the temperature of the reaction around 5° C.;

(3) Removing small aliquots of reaction product hourly and measuring by $H^1$ NMR the formation of the peroxidic species or reaction products;

(4) Stopping the reaction when more than about 50% of the available unsaturated bonds have been reacted;

(5) Diluting the product mixture with dimethylsulfoxide (1:10) to give a solution or dispersion;

(6) Prior to use in the target biological system, a mixture of hematoporphyrin, rose bengal, and methyl-naphthoquinone dry powders was added to the solution or dispersion in sufficient quantity to create a concentration of 20 micromolar of each component dispersed therein when delivered to the target biological system by saline intravenous infusion. Optionally, ascorbate could be added to the formulation prior to use.

EXAMPLE 3

Examples of the Pharmaceutical Formulation

Two preferred formulations are as follows:

| WEIGHT % | INGREDIENT |
| --- | --- |
| 0.54* | Tetraoxane dimer of acetal peroxide from ozonization of geraniol |
| 98.00 | DMSO |
| 0.83 | Hematoporphyrin |
| 0.24 | Methylnaphthoquinone |
| 0.39 | Rose Bengal |

*Determined by mass spectroscopy.

| WEIGHT % | INGREDIENT |
| --- | --- |
| 0.54* | Tetraoxane dimer of acetal peroxide from ozonization of geraniol |
| 98.00 | DMSO |
| 0.83 | Hematoporphyrin |
| 0.24 | Methylnaphthoquinone |
| 0.39 | Chlorophyllin Sodium-Copper Salt |

*Determined by mass spectroscopy.

EXAMPLE 4

Experimental Procedures

To test the effectiveness of the pharmaceutical formulation in reducing insulin resistance, three obese Zucker rats were treated with three different concentrations of the pharmaceutical formulation A.

The obese Zucker rat (fa/fa) is a well-defined animal model for the study of insulin resistance (Czech, et al., 1980; Sherman, et al., 1988; Zucker, et al., 1972). Although basal glucose in early adult life is similar between obese and lean Zucker rats, the obese rat displays severe hyperinsulinemia, glucose intolerance, and an elevated plasma insulin response to a glucose challenge (Cortez, et al., 1991; Zucker, et al., 1972). Muscle insulin resistance is also prominent in obese Zucker rats, as indicated by reduced insulin-stimulated muscle glucose uptake and transport.

The treated Zucker rats were tested for measured glucose tolerance and insulin response to a glucose challenge by an oral glucose tolerance test ("OGTT"). This test was followed by an evaluation of muscle insulin resistance via the hindlimb perfusion technique. Three obese Zucker rats injected with saline served as controls. Rats were fed ad libitum and maintained in a room with a 12 hour light/dark cycle and temperature of 69±1° C.

The pharmaceutical formulation was delivered via an intraperitoneal injection. The dosage was based on the porphoquinone in the pharmaceutical formulation. The first dosage was 0.04 μg/g body weight. This was injected on three consecutive days and followed by an OGTT seven days after the last injection. The second dosage, which was 0.06 μg/g body weight, was injected six days after the OGTT. This was followed with a second oral glucose tolerance test three days later. The final dosage tested was 0.4 μg/g body weight and was injected 13 days after the second OGTT. The volume of pharmaceutical formulation was maintained at approximately 200 μL by dilution with saline. The three OGTT's and the hindlimb perfusion were performed after the rats had fasted 12 hours.

The OGTT consisted of intubating the rats with 500 mg glucose/kg body weight. Glucose was diluted in distilled water and the concentration adjusted so that the volume intubated was between 500 μL and 900 μL. During the OGTT, 0.5 mL blood was sampled from the tail vein of the rats. Blood was drawn prior to and 15, 45, 90, and 120 minutes after glucose intubation. Two drops of blood were immediately used for the determination of blood glucose using a glucometer (One Touch® Basic, Lifescan, Inc., Milpitas, Calif.). The validity and reliability of the glucometer were verified prior to its use in the study by comparing values obtained with the glucometer with those from a YSI 23A glucose analyzer (Yellow Springs Instruments, Yellow Springs, Ohio). Calibration of the glucometer was performed with standards provided by the manufacturer. Once the blood glucose was determined, 0.5 mL of blood was transferred to a tube containing EDTA (24 mg/mL, pH 7.4). The blood was centrifuged and the plasma analyzed for insulin using a radioimmunoassay kit (Linco, St. Louis, Mo.).

The surgical technique used for hindlimb perfusion was in accordance with previously described protocols (Ivy, et al., 1986; Sherman, et al., 1988). Major vessels branching from the abdominal aorta and vena cava, except for the common iliac artery and iliac vein, were ligated. Heparin (100 U) was injected into the inferior vena cava just below the diaphragm. Following the heparin injection, the descending aorta and inferior vena cava were cannulated (Ivy, et al., 1986). Catheters were placed in line with the non-circulating hindlimb perfusion apparatus providing a 37° C., continuously gassed (95% $O_2$/5% $CO_2$) perfusate flow of 6.0 mL/min. Both hindlimbs were perfused during the equilibrium (5 minute) period, then the left iliac artery was ligated so that perfusate flow only moved through the right hindlimb. After the equilibration period, a 25 minute tracer period was used to measure glucose uptake. Perfusate consisted of 6% bovine serum albumin ("BSA") in Krebs-Henseleit buffer ("KHB," pH 7.4) with 0.2 mM pyruvate. During the tracer period, the perfusate contained 6 mM glucose, [1,2-3H] 2-deoxyglucose (0.05 μCi/mL; ICN Biochemicals, Costa Mesa, Calif.) and 0.2 mU/mL insulin (Humulin® R-100, Eli Lilly, Indianapolis, Ind.). Immediately following the perfusion period, the hindlimb was washed out with 35 mL of KHB and the red and white sections of right gastrocnemius and soleus muscle excised, frozen with Wollenberg tongs cooled in liquid $N_2$ and stored frozen (−80° C.) until further analysis.

Hindlimb glucose uptake was determined by multiplying the arterial-venous glucose difference by the perfusate flow rate and made relative to the muscle mass perfused (μg/(g*h)). For the determination of 2-deoxyglucose uptake in individual muscles, a 60-100 mg piece of muscle was dissolved in 1 mL of 1 N KOH by incubating for 15 min at 65° C., mixed, and incubated an additional 5 min at 65° C. An equal volume of 1 N HCl was added to the digested samples, mixed, and aliquots of the neutralized samples counted for [3H] DPM (Beckman LS 6000SC, Fullerton, Calif.). Muscle 2-deoxyglucose uptake was calculated from the specific activity of the original perfusate.

EXAMPLE 5

Body Weight and Food Consumption

The body weight of the rats was recorded daily and food consumption determined for 3 days after the highest pharmaceutical formulation dosage.

Figure 1:
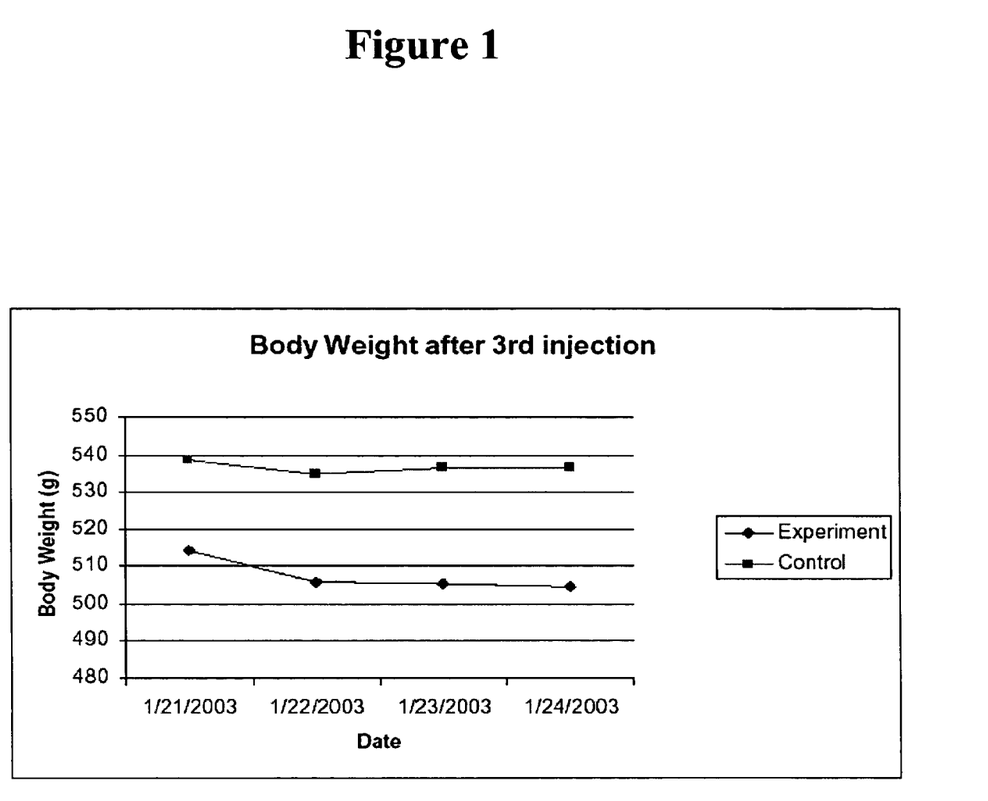
FIG. 1 shows the average body weight of two groups of obese Zucker rats. One group received three injections of the pharmaceutical formulation (Experimental) and one group was treated with saline alone (Control).

At the onset of the experiment, the treated rats weighed an average of 267.7 g and the control rats weighed 266.7 g. At the conclusion of the study, the treated rats weighed 534.3 g and the control rats weighed 557.7 g. Thus, the rats treated with the pharmaceutical formulation gained weight at a slower rate than the controls. FIG. 1 shows the average body weight of the treated rats and the control rats after the third injection of the pharmaceutical formulation.

The adult obese Zucker rat normally eats approximately 25 g of food daily. The food consumption of the control rats was unaffected as they consumed between 21 g to 25 g of food per day. However, for three days after treatment with the final dosage of pharmaceutical formulation, food consumption ranged from 12 g to 19 g per day. Thus, the rats treated with the pharmaceutical formulation also showed a suppression in appetite. The food consumption of the treated rats appeared to increase each day after the injection, indicating that the appetite suppression was not permanent.

EXAMPLE 6

Oral Tolerance Tests

The three OGTT's were performed after the rats had fasted 12 hours.

Figure 2:
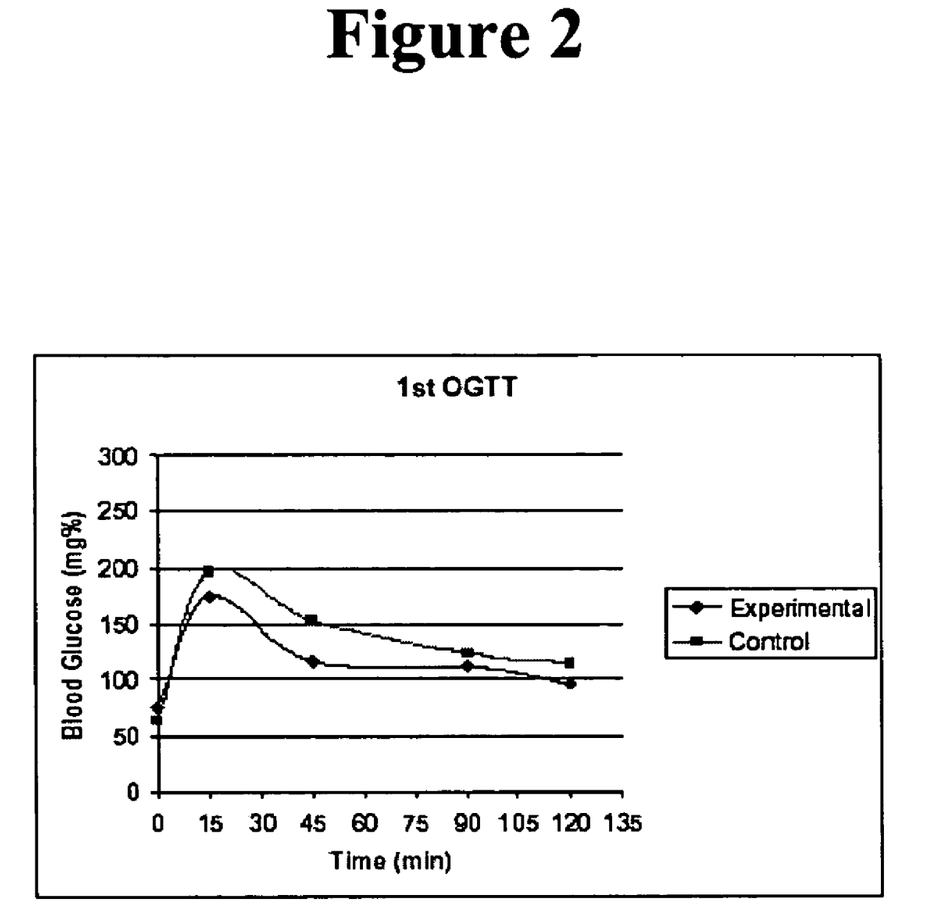
FIG. 2 shows the blood glucose levels of two groups of obese Zucker rats, as measured by an oral glucose tolerance test ("OGTT"). One group received one injection of the pharmaceutical formulation (Experimental) and one group was treated with saline alone (Control).

FIG. 2 shows the blood glucose levels of the treated and control rats during the first OGTT. During the first OGTT, fasting blood glucose concentrations were similar for the treated and the control rats. The increase in blood glucose following glucose intubation, however, was higher in the control rats compared to the treated rats. This increase was evident for a minimum of 45 minutes after the glucose intubation. Plasma insulin levels of the treated rats and control rats were also similar following the overnight fast. Plasma insulin increased significantly in both groups immediately following glucose intubation. However, the insulin response returned to baseline in the treated rats, but remained elevated in the control rats. Thus, despite a lower blood glucose response in the treated rats, their plasma insulin levels were lower during the first OGTT, suggesting an increase in insulin sensitivity.

Figure 3:
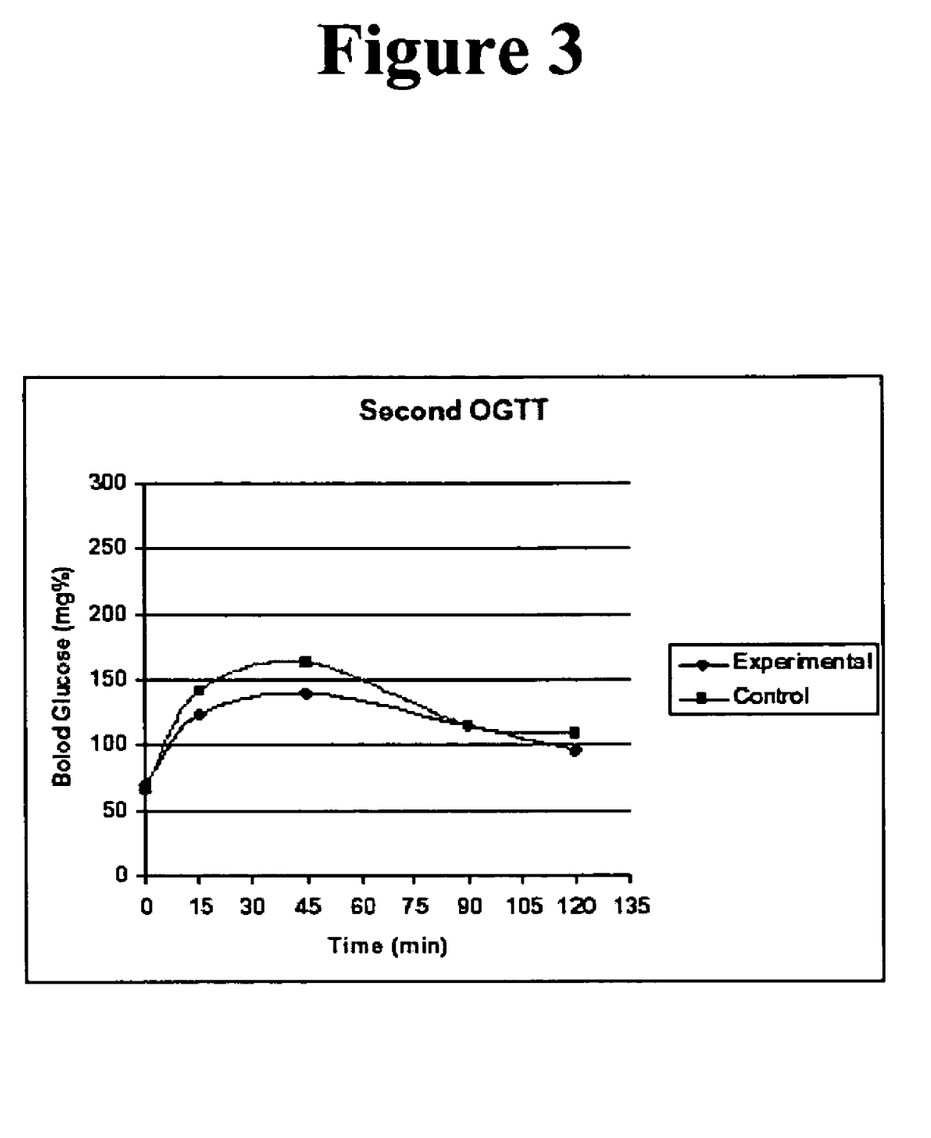
FIG. 3 shows the blood glucose levels of two groups of obese Zucker rats, as measured by an oral glucose tolerance test ("OGTT"). One group received two injections of the pharmaceutical formulation (Experimental) and one group was treated with saline alone (Control).

FIG. 3 shows the blood glucose levels of the treated and control rats during the second OGTT. During the second OGTT, fasting blood glucose concentrations were similar for both groups. Again, the blood glucose response was lower for the treated rats during the first 45 minutes of the OGTT. Although the fasting plasma insulin concentration of the treated rats appeared to be slightly higher than that of the control rats, the rise in insulin following glucose intubation was lower for the treated rats and remained lower during the 2 hour OGTT. There did not appear to be a substantial improvement in the OGTT of the treated rats beyond that produced by the first treatment.

Figure 4:
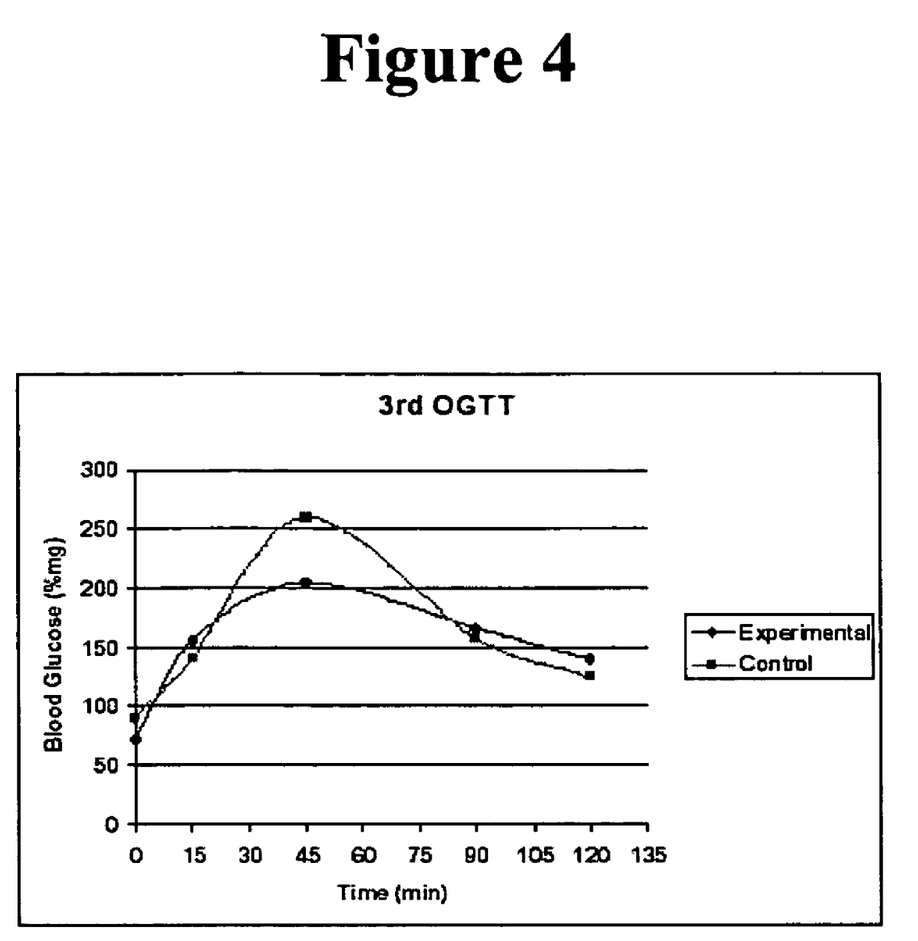
FIG. 4 shows the blood glucose levels of two groups of obese Zucker rats, as measured by an oral glucose tolerance test ("OGTT"). One group received three injections of the pharmaceutical formulation (Experimental) and one group was treated with saline alone (Control).

FIG. 4 shows the blood glucose levels of the treated and control rats during the third OGTT. During the third OGTT, the fasting blood glucose of the controls appeared to have increased, whereas the fasting blood glucose of the treated rats appeared to be similar to previous measures. Following glucose intubation, the glucose response was again lower for the treated rats, but only at 45 minutes after glucose intubation. Fasting plasma insulin levels were similar for the two groups. The insulin response of the treated rats, however, was higher than that of the control rats.

Thus, the results indicate that treatment with the pharmaceutical formulation at 0.04 µg/g body weight for three days resulted in a lowering of the blood glucose response to an oral glucose challenge. Increasing the dosage by 50% or ten-fold did not appear to have an additional effect. The lowering of the blood glucose response occurred despite a lower insulin response in the rats treated with the pharmaceutical formulation. This indicates that the whole body insulin resistance in the obese Zucker rat was improved. The data also indicate that extremely high concentrations of the pharmaceutical formulation are not toxic.

EXAMPLE 7

Hindlimb Perfusion and Muscle Glucose Uptake

Figure 5:
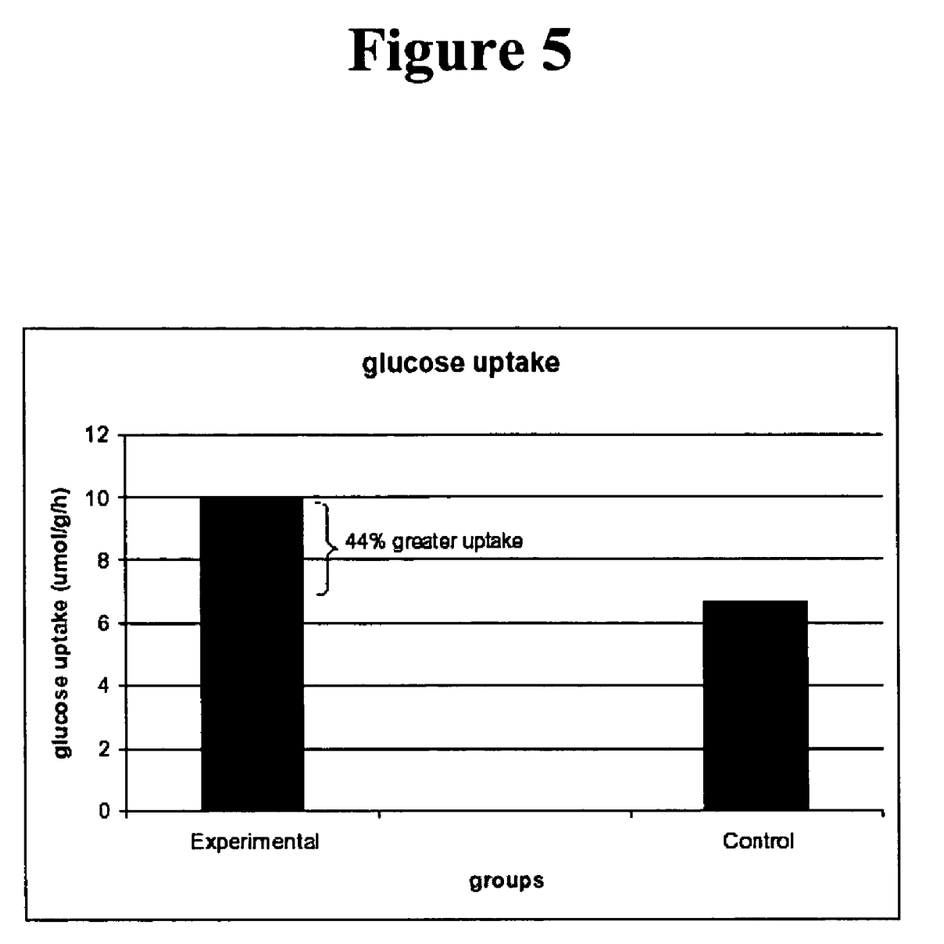
FIG. 5 shows the glucose uptake of two groups of obese Zucker rats, as measured by hindlimb perfusion. One group received three injections of the pharmaceutical formulation (Experimental) and one group was treated with saline alone (Control).

FIG. 5 and Table 7-1 below show the glucose uptake of the treated rats and the control rats, as measured by the hindlimb perfusion technique. Insulin-stimulated glucose uptake was 44% greater in the treated rats compared to the controls. Evaluation of 2-deoxyglucose uptake indicated that the fast-twitch red and white muscle of the rat was more insulin sensitive. There appeared to be no difference in 2-deoxyglucose uptake in the soleus muscle of the two groups.

TABLE 7-1

Average Glucose Uptake

|         |           | mg %    | µmol/g/h |
|---------|-----------|---------|----------|
| Treated | Artery (A)| 148.973 | 125.29   |
|         | Vein (V)  | 137.194 | 115.38   |
|         | A - V     | 11.779  | 9.91     |
| Control | Artery (A)| 148.630 | 120.03   |
|         | Vein (V)  | 140.139 | 113.17   |
|         | A - V     | 8.491   | 6.86     |

REFERENCES CITED

The following U.S. patent documents and publications are hereby incorporated by reference.

U.S. Patents

U.S. Pat. No. 4,451,480 to DeVillez
U.S. Pat. No. 4,591,602 to DeVillez
U.S. Pat. No. 4,983,637 to Herman
U.S. Pat. No. 5,086,076 to Herman
U.S. Pat. No. 5,126,376 to Herman
U.S. Pat. No. 5,190,977 to Herman
U.S. Pat. No. 5,190,979 to Herman
U.S. Pat. No. 5,260,342 to Herman
U.S. Pat. No. 5,270,344 to Herman
U.S. Pat. No. 5,364,879 to Herman Other Publications Cortez, M., C. Torgan, J. J. Brozinick, and J. Ivy. Insulin resistance of obese Zucker rats exercise trained at two different intensities. Am. J. Physiol 261: E613-619, 1991.

Czech, M., M. Prentiki, D. Zaninettie, and J. Jeanrenaud. Insulin resistance in soleus muscle from obese Zucker rats: involvement of several defective sites. Biochem. J. 186: 525-534, 1980.

Ivy, J. L., T. W. Zderic, and D. L. Fogt. Prevention and treatment of non-insulin-dependent diabetes mellitus. E.S.S.R. vol. 27, 1-35, 1999.

Ivy, J., W. Sherman, C. Cutler, and A. Katz. Exercise and diet reduce muscle insulin resistance in obese Zucker rat. Am. J. Physiol 251: E299-305, 1986.

Maritim A. C., R. A. Sanders, J. B. Watkins 3rd. Diabetes, oxidative stress, and antioxidants: A review. J. Biochem. Mol. Toxicol. 17: 24-38, 2003.

Sherman, W., A. Katz, C. Cutler, R. Withers, and J. Ivy. Glucose transport: locus of muscle insulin resistance in obese Zucker rats. Am. J. Physiol. 255: E374-382, 1988.

Zucker, L. M. and H. N. Antoniades. Insulin and obesity in the Zucker genetically obese Rat "fatty." Endocrinology 90: 1320-1330, 1972.

What is claimed is:

1. A method for treating a patient with Type 2 diabetes comprising:

administering to the patient an effective amount of a pharmaceutical formulation comprising:

peroxidic species or reaction products resulting from oxidation of an alkene by an oxygen-containing oxidizing agent, wherein the alkene is selected from the group consisting of α-terpineol, citronellol, nerol, linalool, phytol, geraniol, perillyl alcohol, geranylgeraniol and farnesol, wherein the oxygen-containing oxidizing agent is selected from the group consisting of singlet oxygen, oxygen in its triplet state, superoxide anion, periodate, hydroxyl radical, hydrogen peroxide, alkyl peroxide, carbamyl peroxide, benzoyl peroxide, and oxygen bound to a transition element, and wherein the peroxidic species or reaction products resulting from oxidation of the alkene is from about 0.001% to about 30% by weight of the pharmaceutical formulation;

a penetrating solvent, wherein the penetrating solvent is selected from the group consisting of dimethylsulfoxide, sterol, lecithin, propylene glycol, and methylsulfonylmethane, and wherein the penetrating solvent is from about 50% to about 99% by weight of the pharmaceutical formulation;

a dye containing a chelated divalent or trivalent metal, wherein the dye is selected from the group consisting of porphyrin, rose bengal, chlorophyllin, hemin, corrins, texaphrin, methylene blue, hematoxylin, eosin, erythrosin, lactoflavin, anthracene dye, hypericin, methylcholanthrene, neutral red, fluorescein, phthalocyanine, eumelanin, and pheomelanin, and wherein the dye is from about 0.1% to about 30% by weight of the pharmaceutical formulation; and an aromatic redox compound, wherein the redox compound is selected from the group consisting of substituted or unsubstituted benzoquinone, naphthoquinone, and anthroquinone, and wherein the aromatic redox compound is from about 0.01% to about 20% by weight of the pharmaceutical formulation.

2. The method of claim 1, wherein the alkene is in a liquid form, in a solution, or in a dispersion.

3. The method of claim 1, wherein the alkene is contained in a fixed oil, an ester, a fatty acid, or an ether.

4. The method of claim 1, wherein the oxygen-containing oxidizing agent comprises ozone.

5. The method of claim 1, wherein the penetrating solvent is a liquid, micelle membrane, emollient, or vapor.

6. The method of claim 1, wherein the penetrating solvent is dimethylsulfoxide ("DMSO").

7. The method of claim 1, wherein the dye is selected from the group consisting of porphyrin, rose bengal, chlorophyllin, and a mixture thereof.

8. The method of claim 1, wherein the metal comprises iron.

9. The method of claim 1, wherein the metal is selected from the group consisting of copper, manganese, tin, magnesium, and strontium.

10. The method of claim 1, further comprising an electron donor.

11. The method of claim 10, wherein the electron donor comprises ascorbic acid or a pharmaceutical salt thereof.

12. A method for treating a patient with Type 2 diabetes comprising:

administering to the patient an effective amount of a pharmaceutical formulation comprising:

peroxidic species or reaction products resulting from oxidation of geraniol by a mixture of ozone and oxygen;

dimethylsulfoxide ("DMSO");

a dye containing a chelated divalent or trivalent metal, wherein the dye comprises a mixture of hematoporphyrin and rose bengal or a mixture of hematoporphyrin and chlorophyllin; and methylnaphthoquinone.

* * * * *